United States Patent [19]

Winters et al.

[11] Patent Number: 4,681,122

[45] Date of Patent: Jul. 21, 1987

[54] STEREOTAXIC CATHETER FOR MICROWAVE THERMOTHERAPY

[75] Inventors: Arthur Winters, Short Hills; Casper S. Molee, Bloomfield, both of N.J.

[73] Assignee: Victory Engineering Corp., N.J.

[21] Appl. No.: 779,285

[22] Filed: Sep. 23, 1985

[51] Int. Cl.$^4$ ............................................. A61B 5/02
[52] U.S. Cl. ................................... 128/736; 128/804; 128/784
[58] Field of Search ............ 128/303 B, 303.1, 303.11, 128/303.12, 399, 401, 402, 736, 753, 754, 786, 804

[56] References Cited

U.S. PATENT DOCUMENTS

| | | | |
|---|---|---|---|
| 3,357,431 | 12/1967 | Newell | 128/303 B |
| 3,399,542 | 9/1967 | Howell | 128/736 |
| 3,411,507 | 11/1968 | Wingrove | 128/784 |
| 3,480,003 | 11/1969 | Crites | 128/715 |
| 3,704,705 | 12/1972 | Eckhart | 128/736 |
| 4,058,114 | 11/1977 | Soldner | 128/303 B |
| 4,148,005 | 4/1979 | Larsen et al. | 128/736 |
| 4,253,469 | 3/1981 | Aslan | 128/736 |
| 4,497,324 | 2/1985 | Sullivan et al. | 128/736 |
| 4,557,272 | 12/1985 | Carr | 128/804 X |
| 4,559,951 | 12/1985 | Dahl et al. | 128/786 |
| 4,583,556 | 4/1986 | Hires et al. | 128/804 |

OTHER PUBLICATIONS

R. E. Johnston et al., "Body Tissue Transducer", Jan. 1964, pp. 13-14, IBM Technical Disclosure Bulletin.

*Primary Examiner*—Edward M. Coven
*Attorney, Agent, or Firm*—Cousins & Cousins

[57] ABSTRACT

A multi-lumen catheter that contains two or more independent coaxial sensing elements which can be used for measuring and recording temperature over a wide area at the insertion site. In addition, this catheter can be used for withdrawing blood at its distal port. When a microwave probe is inserted into the proximal lumen and positioned within the catheter, it allows for accurate placement of the microwave field within the area which is temperature monitored.

5 Claims, 4 Drawing Figures

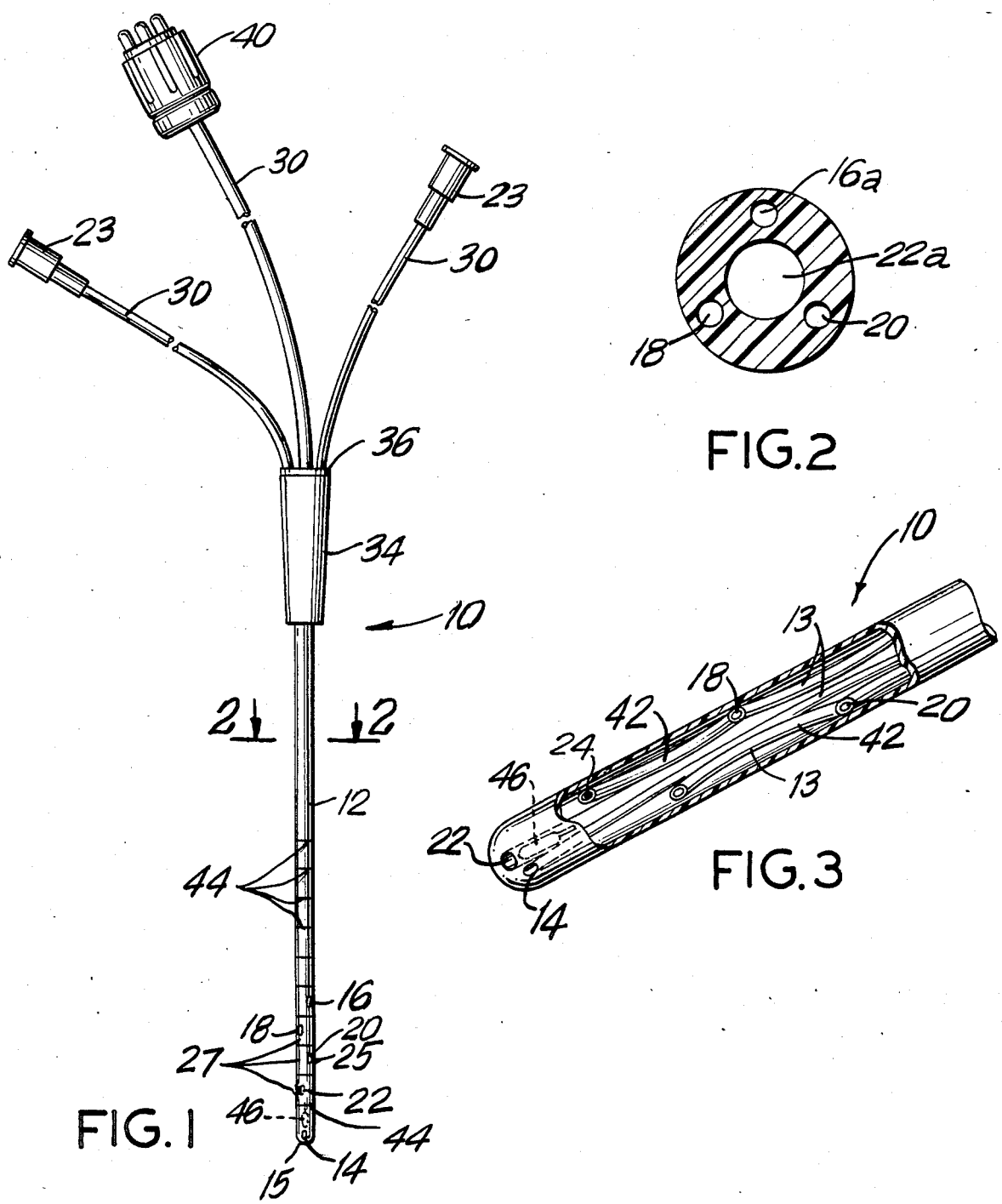
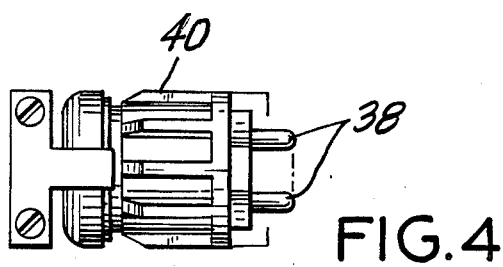

STEREOTAXIC CATHETER FOR MICROWAVE THERMOTHERAPY

FIELD OF THE INVENTION

This invention relates to a stereotaxic multi-sensing, multi-lumen catheter applicator and to a method of treatment using same. More specifically, the invention relates to a catheter for use in treating various brain conditions.

BACKGROUND OF THE INVENTION

Localized thermotherapy is used in a growing number of institutions around the world to treat solid malignant tumors. The therapy consists of heating the tumors to temperatures several degrees centigrade above core temperature (hyperthermic temperatures) and maintaining the tumors at hyperthermic temperatures for a preset period. This procedure is usually repeated several times. Thermotherapy is given either alone or in combination with ionizing radiation or chemotherapy. Clinical results with a variety of malignancies have been encouraging, as described in, for example, Prog. Exp. Tumor Res. 28:198–219, 1984.

Malignant brain tumors are candidates for localized thermotherapy. Such tumors do not metastasize, so that only local control is required. Also, when conventional techniques such as surgery, radiotherapy, or chemotherapy are used to treat malignant brain tumors, the prognosis is usually discouraging. Attempts to treat human brain cancers with thermotherapy date back to 1971, when Sutton in Trans. Am Neurol Assoc. 96:195–199, 1971, reported encouraging results using a combination of thermotherapy induced with an invasive resistive heater and chemotherapy. There was little follow-up to Sutton's work until 1981, when Salcman and Samaras published an article on the biophysical rationale for treating malignant brain tumors with thermotherapy using invasive microwave antennas in Neurosurgery 9:327–335, 1981. Since 1981, a few centers have begun to treat a small number of patients who have malignant brain tumors with localized thermotherapy. (See Prog. Exp. Tumor Res. 28:220–231, 1984.)

The rationale for using microwave-localized thermotherapy for treating malignant brain tumors can be summarized as follows:

1. By using small, invasive applicators, it is possible to guide microwave energy directly into the interior of the malignant brain tumor (see J. Microwave Power 14:339–350, 1979.) Most of the microwave energy broadcast by the antennas of these applicators is absorbed by the tumor tissues, and only a small fraction of the microwave energy usually reaches the healthy tissues surrounding the tumors. The malignant tissues are therefore preferentially heated to higher temperatures than the healthy tissues. Thus, it becomes possble to damage or destroy malignant tissues by heating them to hyperthermic temperatures, while sparing healthy tissues. This preferential damage or destruction of malignant cells by microwave heating is often amplified because malignant cells are often more senstive to insult by heat than are healthy cells. This is because malignant cells, particularly those in the interior of tumors, are often in a state of nutritional deprivation, low pH, and chronic hypoxia (Cancer Res (suppl) 44:4703–4908, 1984). Furthermore, the microvasculature of tumors, being not as well developed and resistant to insult as healthy microvasculature, is more easily damaged by heat than healthy microvasculature (Radiology 137:515–521, 1980). Cells fed by microvasculatures that have been damaged by heat become in turn weakened and more sensitive to heat.

2. Localized thermotherapy enhances the effectiveness of radiotherapy and chemotherapy (Prog. Exp. Tumor Res. 28:198–219, 1984) because (a) thermotherapy interferes with the repair of cells that have been sublethally damaged by radiation; (b) cells in the S phase of the cell cycle which are resistant to ionizing radiation, are very heat-sensitive; (c) hypoxic tumor cells, which tend to be resistant to ionizing radiation and chemotherapy, are especially sensitive to thermotherapy; (d) thermotherapy is effective in oxygenating radioresistant hypoxic cells; and (e) thermotherapy magnifies the cytoxicity of many anticancer drugs.

3. There is evidence that localized thermotherapy stimulates immunological responses (J. Microwave Power 11:168–170, 1976) by causing infiltration of heated tumor sites by macrophages and T lymphocytes (Cancer 43:767–783, 1979). This immunological response can be effective in inhibiting renewed brain tumor growth at the periphery of heated tumors.

STATEMENT OF PRIOR DISCLOSURES

There are several methods that can be used to produce hyperthermic temperatures in brain tissues. These methods include resistive heaters, ultrasound, radiofrequencies and microwaves. The present invention uses microwaves at a frequency of 2450 MHz. This frequency (2450 MHz) is set aside by the Federal Communications Commission for industrial, scientific, and medical applications. This choice was based on the following considerations: (a) 2450 MHz can be efficiently radiated into tumors by short antennas, (b) 2450 MHz can be easily guided into the interior of tumors by means of very thin coaxial cables that do a minimum of damage to healthy brain tissues that must be traversed to reach deep-seated tumors, and (c) thin thermocouples, when properly oriented, are minimally affected by the presence of 2450 MHz fields.

In the past, several commercially available plastic catheters were used for implanting the microwave source and the temperature was monitored by an externally mounted thermocouple. This technique does not allow for accurate measurement or simultaneous measurement over a large area and requires multiple punctures of the area which is to receive microwave radiation, increasing the patient discomfort and increasing the chance of infection or complication.

In an effort to minimize patient discomfort, complications and infection problems and provide the physician with a large area temperature profile, it is preferable that a multi sensing catheter have many temperature monitoring sites converging into one common connector, with a separate opening for the insertion of the microwave source and a separate connection for the distal port.

In microwave hyperthermia, the effective temperature range is extremely narrow and must be carefully monitored and controlled in order that the patient receive the full benefit of the treatment.

It is apparent, therefore, that a single stereotaxic catheter, capable of multiple temperature sensing and providing for blood removal and accurate microwave placement, is very desirable.

OBJECTS AND SUMMARY OF THE INVENTION

It is an object of this invention to provide a multi-sensing, multi-lumen catheter-applicator.

It is a further object of this invention to provide a catheter or applicator adaptable for positioning a microwave source accurately.

A further object is to provide radiopaque markings for X-Ray display to position a catheter.

Another object is to provide in a catheter a lumen from which blood samples can be extracted simultaneously while microwave therapy is carried out.

A further object of the present invention is to provide one electrical connection for multiple sensing elements.

Still another object of the invention is to minimize patient discomfort, decrease the possibility of the associated complications of multiple insertions and reduce the probability of infection and bleeding.

A further object of the invention is to provide a catheter embodying multiple lumens containing a multiple quantity of sensing elements terminating in a common connector and adapted for simultaneous operations, wherein means are provided for identifying individual lumens for their preferred use.

Additional objects and advantages of the invention will become apparent from a consideration of the following detailed description and, in part, will be obvious from the description of the invention.

In its apparatus aspect the invention is a multi sensing catheter which comprises an elongated, plastic, flexible catheter applicator having at least two independent lumens extending through the catheter, with terminations spaced from one another, exiting at, or near, the terminus of the catheter and adapted for connection to a microwave generator or a suitable Luer lock fitting, color coded to suggest use of individual lumens. The catheter has a distal port to withdraw blood.

In its method aspect the invention resides in treating malignant brain tumors by hyperthermic temperatures therein, using microwaves at a frequency of 2450 MHz guided by at least one of the present catheters.

BRIEF DESCRIPTION OF THE DRAWING

In the drawing:

FIG. 1 is a side elevational view of a multi-lumen sensing catheter, constructed in accordance with the preferred form of the invention;

FIG. 2 is an enlarged, cross-sectional view of the tubing and multiple lumens taken on line 2—2 in FIG. 1;

FIG. 3 is an enlarged view, partly in section, depicting the multi lumens and their terminus; and FIG. 4 is a side elevational view of a pin connector for use with the catheter of this invention.

DISCLOSURE OF PREFERRED MODES OF THE INVENTION

Referring to the drawing, a multi-sensing catheter 10, consists of the following elements and is preferably made by the following steps:

1. Cut silicone tubing 12 to the pre-determined length (such as 15 cm.) to form catheter 10.
2. Using a knife, notch the tubing 12 from the distal end 15 at 0.5 cm, 1.5 cm, 2.5 cm, 3.5 cm, 5.5 cm. Notches 16, 18, 20, 22 must be 180 degrees in an alternating pattern from each other. The notch size is about 0.100 inch long.
3. Insert a 0.015 inch silicon plug (not shown) into the distal portion of each notch, using an adhesive such as a cyanoacrylate adhesive to seal the plug into position.
4. Pull from distal end of each notch of catheter 10 a thermistor bead 24 into each of the notches 16, 18, 20, 22. As shown in FIG. 3 and using an adhesive such as a cyanoacrylate, position and seal each thermistor into the center-bottom of each of the lumens 13. Allow to air dry. Fill notches sufficiently with a glue such as an epoxy glue to give a smooth and continuous feel to the tubing. Allow the assembly to air dry.
5. Using a flare tool, expand the proximal end of lumen 22a as shown in FIG. 2 and insert a distal extension tubing with a locking connector such as a Luer lock 23 (FIG. 1), using adhesive to seal the extension tubing in place. Allow to air dry.
6. Using a flare tool, expand lumens 18, 20, at proximal end and pull all extraneous electrical wires through extension tubing 30. Insert electrical extension tubing into flared area. Use adhesives to seal in place. Allow to air dry.
7. Using a flare tool, expand lumen 16a at its proximal end. Insert extension tubing 30 terminating into a Luer lock 23 and seal in place with adhesive. Allow to air dry.
8. Apply sufficient epoxy or other glue around all joint areas and allow to air dry for 24 hours.
9. As shown in FIG. 1, position a protective shroud 34 over epoxied interconnect area, apply adhesive at distal end of shroud 34. Shroud 34 serves as a reservoir to be filled with epoxy or other adhesive to give strength to the extension connections to the main body. Allow to air dry. Apply adhesive to inner edge of cap 36 and snap shut. Allow to air dry.
10. Solder attached thermistor wires 42 to pins 38 of multi-pin connector 40 (see FIG. 4).
11. Using radiopaque marking material such as gold or tantalum, calibrate the catheter 10 from the distal end 15 every centimeter for a length of 10 centimeters, as shown in FIG. 1. The resulting markers 44 serve to indicate the depth of penetration of the catheter so that the same can be recorded for future use.
12. Insert the catheter 10 into a stirred, 47° C., sterile water bath and test each thermistor for proper electric value.

The invention is further illustrated by the following examples of use thereof in humans to administer thereto thermotherapy.

Brain tumors in 12 patients were heated with one or more of the miniature coaxial applicators (antennae) 46 of FIGS. 1 and 3. Fischer cannulas were stereotaxically positioned with their tips inside the tumors to be treated, and the applicators were inserted in the cannulas. An array plug such as that disclosed and claimed in coassigned copending application Ser. No. 779,170, filed Sept. 23, 1985, and incorporated herein by reference was inserted into a burr hole in the skull of the patient and used to position the cannulas. In some instances, the volume of tissues treated with a given antenna in a given cannula was doubled by heating first with the antenna inserted all the way into the cannula and then by treating again after withdrawing the antenna by approximately 2 cm. All procedures were done under local anesthesia combined with analeptic medication. Blood could be drawn through distal opening 14 with a syringe.

During the thermotherapy sessions, the microwave power to the applicators was adjusted continuously to maintain the readings of the thermocouples on the applicators at 45° C. Based on in vivo dog experiments, the corresponding highest tumor temperature was approximately 42.5° C. This adjustment method of estimating maximal tumor temperature was sufficiently accurate for effective therapy. The alternative of directly measuring tumor temperatures by inserting additional catheters with thermocouples into the tumors was rejected because of the damage to healthy brain tissues that would have been caused by the tracks of these catheters.

All tumors were heated for approximately one hour during each thermotherapy session.

During the thermotherapy session, as well as during most other thermotherapy sessions, the microwave power required to maintain constant tumor temperature decreased as the session progressed. This decrease in the microwave power required to maintain constant tumor temperature is most likely due to a reduction in tumor blood flow (TBF) caused by the thermotherapy. (Most of the heat generated by microwaves in tumors is usually removed by the TBF.) Decreases in TBF during and after heating tumors to hyperthermic temperatures have been observed in animals, where heating tumors to 43° C. produced petechiae, stasis, occasional thrombosis, some endothelial degeneration, and persistent hyperemia. Histopathological studies of human malignant tumors after thermotherapy reveal significant changes in the tumor stroma. Stromal blood capillary walls are massively infiltrated with round cells and undergo degenerative changes leading to necrosis and obliteration of the vascular supply of the tumor.

RESULTS OF THE THERMOTHERAPY WITH CATHETER OF THE INVENTION

Twelve patients with malignant brain tumors who had failed to respond to conventional therapies were treated with thermotherapy. Hyperthermic temperatures (43° C.) were induced in the tumors using microwaves at a frequency of 2450 MHz that were guided into the tumors by one or more semirigid applicators of this invention. During each treatment, the tumors were maintained at hyperthermic temperatures for one hour. Several treatments spaced a few days apart were usually administered. The procedure used for producing hyperthermia in brain tumors with microwaves proved to be safe and could be repeated several times without producing toxic effects. Objective tumor responses were obtained in 75% of the patients (decrease in tumor size, 3 patients; slowing of tumor growth, 2 patients; necrosis of tumor tissues verified by pathological examination, 4 patients). Also, in all patients, the microwave power required to heat for a given time or a given volume decreased during most of the thermotherapy sessions, possibly because of heat damage to the tumor vasculature. These results indicate that thermotherapy is a promising modality for treating malignant brain tumors, either as the sole therapy or in combination with radiotherapy and chemotherapy.

Intractable headaches were reduced in 5 of 12 patients (Cases 1, 2, 3, 7 and 10). When headaches recurred, they were less severe and were manageable with minimal medication. Neurological function improved in 5 of 12 patients. In Case 11, speech improved. In Cases 1 and 4, there was increased strength in the right arm. In Case 11, there was improved comprehension, and in Case 12, there was an increased state of alertness. In Cases 3 and 10, there was decreased mental confusion.

No adverse effects due to repeated microwave thermotherapy treatments were observed. Unlike the situation with radiation or chemotherapy, there do not seem to be toxic limits to repeated thermotherapy. The microwave power required to maintain a constant tumor temperature decreased during many of the treatment sessions, possibly indicating progressive damage to the tumor vascular system. Microwave thermotherapy can be performed with a minimum of difficulty, and the applicator can be positioned precisely with stereotaxic manipulation. Advantageously, the herein described procedure requires less time to perform than a formalized craniotomy.

What is claimed is:

1. Apparatus for microwave thermotherapy comprising:
   a catheter;
   said catheter being insertable into living tissue;
   at least first and second lumens extending along a substantial axial distance within said catheter;
   said first and second lumens each including a proximal end and a distal end;
   said distal end of each of said first and second lumens being sealed;
   said proximal end of each of said first and second lumens including means for permitting the passage of electrical conductors therethrough;
   a microwave antenna positionable within said first lumen, and effective, when said catheter is inserted into living tissue, and said microwave antenna is energized with microwave energy, for increasing a first temperature of a portion of said living tissue in a vicinity of said catheter; and
   a temperature sensor positionable within said second lumen and effective for measuring a second temperature within said second lumen related to said first temperature, whereby said microwave energy may be controllable to maintain said first temperature within predetermined limits.

2. Apparatus according to claim 1, further comprising:
   at least a third lumen having a proximal end and a distal end; and
   said proximal and distal ends both being open whereby materials may be transported into and out of said living tissue in a vicinity of said portion of said living tissue.

3. Apparatus according to claim 1, further comprising;
   at least one radiopaque marker at a predetermined location on said catheter; and
   said predetermined location having a predetermined relationship to a location of said microwave antenna.

4. Apparatus according to claim 1 wherein said temperature sensor is a thermistor.

5. Apparatus for microwave thermotherapy comprising:
   a catheter;
   said catheter being insertable into living tissue;
   at least first and second lumens extending along a substantial axial distance within said catheter;
   said first and second lumens each including a proximal end and a distal end;

said distal end of each of said first and second lumens being sealed;

said proximal end of each of said first and second lumens including means for permitting the passage of electrical conductors therethrough;

a microwave antenna positionable within said first lumen, and effective, when said catheter is inserted into living tissue, and said microwave antenna is energized with microwave energy, for increasing a first temperature of a portion of said living tissue in a vicinity of said catheter;

a temperature sensor positionable within said second lumen and effective for measuring a second temperature within said second lumen related to said first temperature, whereby said microwave energy may be controllable to maintain said first temperature within predetermined limits;

at least a third lumen having a proximal end and a distal end;

said proximal and distal ends of said third lumen both being open whereby materials may be transported into and out of said living tissue in a vicinity of said portion of said living tissue;

at least one radiopaque marker at a predetermined location on said catheter; and said predetermined location having a predetermined relationship to a location of said microwave antenna.

* * * * *